United States Patent

Stoss et al.

[11] Patent Number: 5,254,570
[45] Date of Patent: Oct. 19, 1993

[54] ACYL DERIVATIVE OF DIANHYDROHEXITOLS

[75] Inventors: Peter Stoss; Matyas Leitold, both of New York, N.Y.

[73] Assignee: Pfizer Inc., New York, N.Y.

[21] Appl. No.: 411,345

[22] Filed: Sep. 20, 1989

[30] Foreign Application Priority Data

Sep. 20, 1988 [DE] Fed. Rep. of Germany ....... 3831949

[51] Int. Cl.$^5$ .............................................. A61K 31/44
[52] U.S. Cl. ................................................... 514/337
[58] Field of Search ................................ 514/338, 337

[56] References Cited

FOREIGN PATENT DOCUMENTS 0114270 8/1984 European Pat. Off. .
0207397 6/1986 European Pat. Off. .
0207398 6/1986 European Pat. Off. .

OTHER PUBLICATIONS

Chemical Abstracts, vol. 102, 1985, 149715u.
Chemical Abstracts, vol. 107, 1987, 102646k.
Chemical Abstracts, vol. 107, 1987, 121085t.

Primary Examiner—S. J. Friedman
Attorney, Agent, or Firm—Peter C. Richardson; Paul H. Ginsburg; Garth Butterfield

[57] ABSTRACT

The present invention relates to a pharmaceutical composition comprising: (a) a compound of the formula

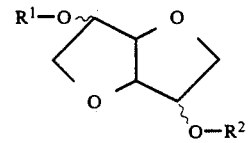

wherein $R^1$ and $R^2$ are as defined below; and (b) isosorbide 5-mononitrate or isosorbide 2-mononitrate or glycerol trinitrate or glycerol 1-mononitrate or glycerol 2-mononitrate: and, optionally (c) a pharmaceutically acceptable carrier. The composition is useful in the prevention and treatment of cardiovascular diseases, and is especially useful in the prevention and treatment of angina pectoris and myocardial infarction.

6 Claims, No Drawings

ACYL DERIVATIVE OF DIANHYDROHEXITOLS

The invention relates to a pharmaceutical composition for preventing and treating cardiovascular diseases, especially for preventing and treating myocardial infarction.

German OffenLegungsschrift 3,248,548 (EP-A 114,270) discloses new acyl derivatives of 1,4:3,6-dianhydrohexitols which can be used as peripheral and central vasodilators and as coronary therapeutics. These compounds are dihydropyridylcarbonyl derivatives.

Nitro derivatives such as isosorbide 5-mononitrate (5-ISM), isosorbide 2-mononitrate (2-ISM), glycerol trinitrate (GTN), glycerol 1-mononitrate (1-GMM) and glycerol 2-mononitrate (2-GMN) have long been known as vasodilating and coronary therapeutic pharmaceuticals.

It has now been found that the specific above-mentioned acyl derivatives of 1,4:3,6-dianhydrohexitols exhibit, when combined with the coronary therapeutic nitro derivatives, surprising effects not observed prior to this invention, which are extremely therapeutically important and desired, including, especially, a significant reduction of the myocardial infarction rate.

German OffenLegungsschrift 3,523,544 (EP-A-207,398) discloses a solid combination product which contains nifedipine and isosorbide 5-mononitrate (5-ISM) and can be used for the long-term treatment of heart diseases, especially diseases of the coronaries and of the myocardium. There is no mention therein of a reduction in the myocardial infarction rate.

German OffenLegungsschrift 3,523,540 (EP-A-207,397) discloses combination products of certain dihydropyridines with 5-ISM, which are likewise suitable for controlling heart diseases. Nisoldipine and nitrendipine are disclosed therein as preferred dihydropyridines. These known combinations are said to prevent the development of tolerance to the nitrate component and to reduce undesired side effects. An intentional reduction in the myocardial infarction rate is not disclosed.

Although the acyl derivatives used in the combination products according to the invention also contain the dihydropyridyl radical, their structures differ considerably from nifedipine on the one hand and the dihydropyridines such as nisoldipine and nitrendipine on the other hand.

SUMMARY OF THE INVENTION

The present invention relates to pharmaceutical compositions comprising:
(a) a compound of the formula I

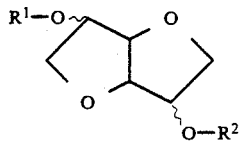

wherein
$R^1$ is hydrogen, a lower acyl radical having 2 to 5 carbon atoms, a pyridylcarbonyl radical or nitro; and
$R^2$ is a 1,4-dihydropyridylcarbonyl radical of the general formula II

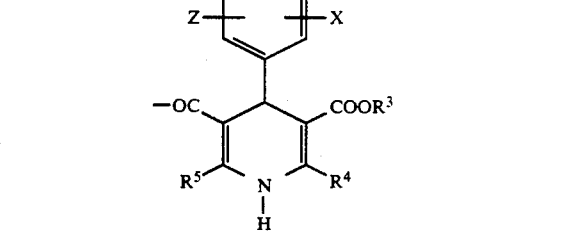

wherein X, Y, and Z are each independently selected from the group consisting of hydrogen, ($C_1$–$C_6$) alkoxy, ($C_1$–$C_6$) alkyl, cyano, dialkylamino, chloro, bromo, fluoro, iodo, nitro, trifluoromethyl, and methylenedioxy, with the proviso that no more than one of X, Y, and Z is methylenedioxy;
$R^3$ is a straight-chain or branched, saturated or unsaturated hydrocarbon radical having 1 to 5 carbon atoms, wherein the carbon chain of said hydrocarbon radical may optionally be interrupted by an oxygen atom and wherein said hydrocarbon radical may optionally be substituted with one cyano group; and
$R^4$ and $R^5$ are ($C_1$–$C_6$) alkyl;
or a pharmaceutically acceptable salt of said compound of formula I;

(b) isorbide 5-mononitrate (5-ISM) or isosorbide 2-mononitrate (2-ISM) or glycerol trinitrate (GTN) or glycerol 1-mononitrate (1-GMN) or glycerol 2-mononitriate (2-GMN), in a ratio by weight of components (a) and (b) of a:b equalling from about 8:1 to about 1:80, and preferably from about 3:1 to about 1:8;
and, optionally,
(c) a pharmaceutically acceptable carrier.

The invention also embraces a process for preparing said pharmaceutical compositions, comprising mixing:
(a) a compound of the formula I or a pharmaceutically acceptable salt thereof:
(b) 5-ISM or 2-ISM or GTN or 1-GMN or 2-GMN, in a ratio by weight of components (a) and (b) of a:b equalling from about 8:1 to about 1:80, and preferably from about 3:1 to about 1:8;
and, optionally,
(c) a pharmaceutically acceptable carrier.

The invention further relates to a method of treating or preventing a cardiovascular disease such as angina pectoris or myocardial infarction in a mammal, including a human, comprising administering to a mammal an amount of a pharmaceutical composition comprising:
(a) a compound of the formula I or a pharmaceutically acceptable salt thereof:
(b) 5-ISM or 2-ISM or GTN or 1-GMN or 2-GMN; in a ratio by weight of components (a) and (b) of a:b equalling from about 8:1 to about 1:80:
and, optionally,
a pharmaceutically acceptable carrier.

The compounds of the formula I may contain chiral centers and may therefore exist in different stereoisomeric forms. This invention relates to pharmaceutical compositions containing any of the isomers of compounds of the formula I, or mixtures thereof.

DETAILED DESCRIPTION OF THE INVENTION

The preparation of the compounds of the general formula I is described in German OffenLegungsschrift 3,248,548.

The substituents —$OR^1$ and $OR^2$ in the compounds of the general formula I can be both exo- and endo-linked to the ring system. This is expressed in the formula I by a wavy line (---), thus including derivatives both of isomannide (endo/endo), isosorbide (endo/exo) and isoidide (exo/exo).

Cations for pharmaceutically acceptable salts embrace sodium, potassium, lithium, calcium, magnesium, ammonium and organic amines.

The pharmaceutical compositions of this invention can be administered in from one to four dosages per day, each dosage containing from about 1 to about 400 mg of a compound of the formula I. However, the dosage should be established in the individual case as a function of the severity of the disease, and the weight and constitution of the patient, as well as other relevant factors, by the administering physician. Those combinations which contain 5-40 mg of the compounds of the formula I and 10-40 mg of 5-ISM or 10-40 mg of 2-ISM or 5-20 mg of GTN or 20-100 mg of 1-GMN or 50-400 mg of 2-GMN are of particular interest.

Pharmaceutical compositions are to be understood to be those which contain the active substance or the active substance combination, where appropriate with customary inactive ingredients and vehicles, in a form which can be administered to the patients. Particularly preferred in the present case are solid and liquid pharmaceutical formulations which can be administered orally.

The active substances according to this invention can be administered alone, but as a rule they are administered mixed with a suitable pharmaceutical excipient or diluent, which is selected taking account of the route of administration. The active substances are preferably administered orally, for example, in the form of tablets containing vehicles such as, for example, starch or lactose, or in capsules in the form of solutions or suspensions in customary pharmaceutical inactive ingredients which can additionally contain flavorings or colorings. On administration to animals, the active substances are normally added to the animal feed or the drinking water.

The pharmaceutical compositions according to this invention are outstandingly suitable for controlling cardiovascular diseases of a wide variety of types. It is true that the individual components, namely both the compounds of the general formula I as well as 5-ISM, 2-ISM, GTN, 1-GMN and 2-GMN, are also known to act in this area. However, an unexpected advance is achieved with the new active substance combinations in that new types of action are exhibited which are not intrinsic to the individual components. Desired properties are enhanced and undesired are suppressed. Thus, an alteration in the spectrum of action results from the combination of components, and a synergistic effect of very great therapeutic significance is achieved.

It has emerged, in particular, that it is possible, surprisingly, to bring about a distinct reduction in the myocardial infarction rate with the pharmaceutical compositions of the invention. Hence, these combinations can be used as pharmaceuticals for the prevention and treatment of myocardial infarction. This provides a new method of preventing and treating angina pectoris, where it has not hither-to been possible to employ calcium antagonists of the 1,4-dihydropyridine type for this purpose because activity is lacking.

In addition to the synergistic effect and the new effectiveness in preventing and treating myocardial infarction, the compounds of the general formula I are distinguished by favourable toxicity data. Thus, compound A which is used in the example is distinctly superior to nifedipine, as is evident from Table 2 hereinafter.

Owing to distinctly lower toxicity and the synergism, the active substance combinations according to the invention are also especially suitable for the long-term treatment of the above-mentioned diseases. Furthermore, they bring about a lowering both of the preload and of the afterload on the heart, which represents a great advantage and a significant advance in therapy. Another surprising and extremely desirable property of the pharmaceutical compositions of the present invention is that they rarely cause an increase in heart rate. In this respect they are distinctly superior to nifedipine and nitrendipine. Moreover, a distinct prolongation of the duration of action is achieved with the combinations according to the invention by comparison with the individual components thereof.

The following examples further illustrate, but do not limit the present invention.

EXAMPLE 1

10 g of a compound of the general formula I are mixed with 10 g of 5-ISM (50% in lactose), a further 20 g of lactose, and 25 g of maize starch and 15 g of microcrystalline cellulose and granulated as usual. The resulting granules are compressed to give tablets of various sizes, and thus various contents of active substance, or are used to fill gelatin capsules of various capacities, and thus different contents of active substance.

EXAMPLE 2

15 g of a compound of the general formula I are mixed with 100 g of a 5 per cent trituration of GTN in lactose and 50 g of maize starch and granulated as familiar to all those skilled in the art. The dried and screened granules are mixed with 10 g of sodium stearyl fumarate and 50 g of talc and compressed to form tablets of various sizes or used to fill gelatin capsules of various sizes.

We claim:

1. A pharmaceutical composition used for the prevention and treatment of cardiovascular disease comprising:

(a) a compound of formula I

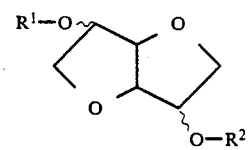

wherein $R^1$ is hydrogen, a ($C_1$-$C_6$) acyl radical having 2 to 5 carbon atoms, a pyridylcarbonyl radical or nitro; and $R^2$ is a 1,4-dihydropyridylcarbonyl radial of the general formula II

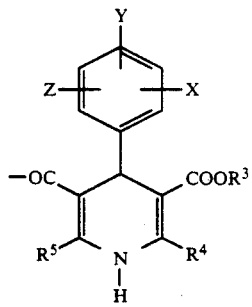

wherein X, Y, and Z are each independently selected from from the group consisting of hydrogen ($C_1$–$C_6$) alkoxy, ($C_1$–$C_6$) alkyl, cyano, dialkylamino, chloro, bromo, fluoro, iodo, nitro trifluoromethyl, and methylenedioxy, with the proviso that no more than one of X, Y, and Z is methylenedioxy;

$R^3$ is a straight-chain or branched, saturated or unsaturated hydrocarbon radical having 1 to 5 carbon atoms, wherein the carbon chain of said hydrocarbon radical may optionally be interrupted by an oxygen atom and wherein said hydrocarbon radical may optionally be substituted with one cyano group; and $R^4$ and $R^5$ are ($C_1$–$C_6$) alkyl;

or a pharmaceutically acceptable salt of said compound of formula I;

(b) isosorbide 5-mononitrate (5-ISM) or isosorbide 2-mononitrate (2-ISM) or glycerol trinitrate (GTN) or glycerol 1-mononitrate (1-GMN) or glycerol 2-mononitrate (2-GMN), in a ratio by weight of said component (a) to said component (b) of from about 8:1 to about 1:80;

and, optionally, (c) a pharmaceutically acceptable carrier.

2. A pharmaceutical composition according to claim 1, comprising said components (a) and (b) in a ratio by weight of (a) to (b) equalling from about 3:1 to about 1:8.

3. A pharmaceutical composition according to claim 1, comprising 5–40 milligrams of a compound of the formula I, or a pharmaceutically acceptable salt thereof, per either 10–40 milligrams of 5-ISM or 10–40 milligrams of 2-ISM or 5–20 milligrams of GTN or 20–100 milligrams of 1-GMN or 50–400 milligrams of 2-GMN.

4. A pharmaceutical composition according to claim 1, wherein $R^1$ is hydrogen or a nitro group.

5. A pharmaceutical composition according to claim 1, wherein said component (a) is (−)-5-[1,4-dihydro-1,6-dimethyl-3-methoxycarbonyl-4-(3-nitrophenyl)-5-pyridylcarbonyl]isosorbide.

6. A method of treating or preventing a cardiovascular disease such as angina pectoris, myocardial infarction or another cardiovascular disease that can be treated or prevented by the administration of a vasodilating agent or an agent effective in lowering the preload and afterload on the heart in a mammal, comprising administering to said mammal an amount of a pharmaceutical composition according to claim 1 effective in treating or preventing such disease.

* * * * *